(12) United States Patent
Roscoe et al.

(10) Patent No.: US 8,936,916 B2
(45) Date of Patent: Jan. 20, 2015

(54) POLYPEPTIDES FOR MICROBIAL DETECTION

(71) Applicant: 3M Innovative Properties Company, St. Paul, MN (US)

(72) Inventors: Stephen B. Roscoe, Woodbury, MN (US); Stephanie J. Moeller, Stillwater, MN (US); Yi He, Roseville, MN (US); Richard B. Ross, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 6 days.

(21) Appl. No.: 13/932,507

(22) Filed: Jul. 1, 2013

(65) Prior Publication Data

US 2013/0309693 A1    Nov. 21, 2013

Related U.S. Application Data (62) Division of application No. 12/867,078, filed as application No. PCT/US2009/033903 on Feb. 12, 2009, now Pat. No. 8,497,353.

(60) Provisional application No. 61/028,896, filed on Feb. 14, 2008.

(51) Int. Cl.
  *G01N 33/53* (2006.01)
  *G01N 33/569* (2006.01)
  *C07K 7/08* (2006.01)

(52) U.S. Cl.
  CPC ...... *G01N 33/56961* (2013.01); *G01N 2469/10* (2013.01); *C07K 7/08* (2013.01)
  USPC ........................................................ 435/7.2

(58) Field of Classification Search
  USPC ........................................................ 435/7.2
  See application file for complete search history.

(56) References Cited

U.S. PATENT DOCUMENTS

| | | | |
|---|---|---|---|
| 4,483,929 A | 11/1984 | Szoka | 436/533 |
| 4,874,710 A | 10/1989 | Piran | 436/518 |
| 5,089,413 A | 2/1992 | Nelson et al. | 435/254 |
| 5,266,461 A | 11/1993 | Tanaka | 435/7 |
| 5,776,487 A | 7/1998 | Wilson et al. | 424/450 |
| 6,225,046 B1 | 5/2001 | Vesey et al. | 435/5 |
| 6,294,321 B1 | 9/2001 | Wakshull et al. | |
| 6,743,638 B1 | 6/2004 | Tsilosani et al. | 436/518 |
| 6,770,453 B1 | 8/2004 | Potts et al. | 435/18 |
| 7,141,387 B2 | 11/2006 | Ushiyama | 435/34 |
| 2002/0107179 A1 | 8/2002 | Potts et al. | 514/8 |
| 2004/0063905 A1 | 4/2004 | Aojula et al. | |
| 2006/0183166 A1 | 8/2006 | Mayer et al. | 435/7 |
| 2007/0031965 A1 | 2/2007 | Rider | 435/325 |
| 2007/0099234 A1 | 5/2007 | Zhang et al. | 435/7 |
| 2007/0207209 A1 | 9/2007 | Murphy et al. | |

FOREIGN PATENT DOCUMENTS

| EP | 0 106 370 | 4/1984 | G01N 33/54 |
|---|---|---|---|
| WO | WO 97/33908 | 9/1997 | C07K 7/08 |
| WO | WO 98/41535 | 9/1998 | |
| WO | WO 99/20252 | 4/1999 | A61K 9/127 |
| WO | WO 02/059147 | 8/2002 | C07K 14/00 |
| WO | WO 2009/102824 | 8/2009 | G01N 33/53 |
| WO | WO 2009/102859 | 8/2009 | C07K 9/00 |

OTHER PUBLICATIONS

Aliphatic Amino Acids data sheet, 1 page, 2003.
Guenther, J.F. et al.; "Phosphorylation of Soybean Nodulin 26 on Serine 262 Enhances Water Permeability and is Regulated Developmentally and by Osmotic Signals"; The Plant Cell; vol. 15; 2003; pp. 981-991.
Leippe, M. et al.; "Pore-forming peptide of pathogenic *Entamoeba histolytica*"; Proc. Natl Acad. Sci.; vol. 88; 1991; pp. 7659-7663.
Akramiene D. et al.; "Effects of beta-glucans on the immune system"; Medicina (Kaunas); vol. 43, No. 8; (2007) pp. 597-606.
Amiche, M. et al.; "Isolation of dermatoxin from frog skin, an antibacterial peptide encoded by a novel member of the dermaseptin genes family"; Eur. J. Biochem.; vol. 267, No. 14; (2000); pp. 4583-4592.
Amiche, M. et al.; "A consistent nomenclature of antimicrobial peptides isolated from frogs of the subfamily Phyllomedusinae"; Peptides; vol. 29; (2008) pp. 2074-2082.
de la Rosa, G. et al.; "Regulated recruitment of DC-SIGN to cell-cell contact regions during zymosan-induced human dendritic cell aggregation"; Journal of Leukocyte Biology; vol. 77; (2005) pp. 699-709.
Di Carlo, F.J. et al.: "On the Composition of Zymosan" Science; vol. 127; (1958) pp. 756-757.
Dillon, S. et al.; "Yeast zymosan, a stimulus for TLR2 and dectin-1, induces regulatory antigen-presenting cells and immunological tolerance"; The Journal of Clinical Investigation; vol. 116, No. 4; (2006) pp. 916-928.
Haga, M. et al.; Analytical Biochemistry; vol. 118; (1981); pp. 286-293.
Le Cabec, V. et al.; "Nonopsonic Phagocytosis of Zymosan and *Mycobacterium kansasii* by CR3 (CD11b/CD18) Involves Distinct Molecular Determinants and is or is not Coupled with NADPH Oxidase Activation"; Infection and Immunity; vol. 68, No. 8; (2000); pp. 4736-4745.
Li, W. et al.; GALA: a designed synthetic pH-responsive amphipathic peptide with applications in drug and gene delivery; Advanced Drug Delivery Reviews; vol. 56; (2004); pp. 967-985.
Miura, T. et al.; "Antigen-specific response of murine immune system toward a yeast β-glucan preparation, zymosan"; FEMS Immunology and Medical Microbiology; vol. 24; (1999): pp. 131-139.

(Continued)

*Primary Examiner* — Bin Shen (57) ABSTRACT

Polypeptides which can be activated to cause the formation of pores in a lipid membrane are disclosed. Also disclosed are polypeptide compositions for the detection of target microorganisms and methods of using said compositions.

6 Claims, 3 Drawing Sheets

(56) References Cited

OTHER PUBLICATIONS

Ozinsky A. et ai.; "The repertoire for pattern recognition of pathogens by the innate immune system is defined by cooperation between toll-like receptors"; Proc Natl Acad Sci USA; vol. 97, No. 25; (2000); pp. 13766-13771.

Rongen, H.A.H. et al.; "Review article—Liposomes and immunoassays"; Journal of Immunological Methods; vol. 204 (1997) pp. 105-133.

Sato, M. et al.; "Direct Binding of Toll-Like Receptor 2 to Zymosan, and Zymosan-Induced NF-κB Activation and TNF-α Secretion are Down-Regulated by Lung Collection Surfactant Protein $A^1$"; The Journal of Immunology; vol. 171; (2003) pp. 417-425.

Underhill D.M. et al.; "The Toll-like receptor 2 is recruited to macrophase phagosomes and discriminates between pathogens"; Nature; vol. 401; (1999); pp. 811-815.

Fmoc Solid Phase Peptide Synthesis—A Practical Approach; W.C. Chan and P.D. White, eds., Oxford University Press, New York, NY: 2000; Title, copyright and table of contents consisting of 9 pgs.

Antibodies—A Laboratory Manual; E. Harlow and D. Lane, eds: 1988 Cold Spring Harbor Laboratory Press, Cold Spring Harbor, NY; Title, copyright and table of contents consisting of 9 pgs.

Willment, J.A. et al.; "Characterization of the Human β-Glucan Receptor and its Alternatively Spliced Isoforms"; The Journal of Biological Chemistry' vol. 276, No. 47; 2001; pp. 43818-43823.

Pierre. T. et al,; "Phylloxin, a novel peptide antibiotic of the dermaseptin family of antimicrobial/opioid peptide precursors"; Eur. J. Biochem; vol. 267; 2000; pp. 370-378.

SEQUENCE LISTING

<160> NUMBER OF SEQ ID NOS: 4

<210> SEQ ID NO 1
<211> LENGTH: 19
<212> TYPE: PRT
<213> ORGANISM: Phyllomedusa bicolor

<400> SEQUENCE: 1

Gly Trp Met Ser Lys Ile Ala Ser Gly Ile Gly Thr Phe Leu Ser Gly
1               5                   10                  15

Met Gln Gln

<210> SEQ ID NO 2
<211> LENGTH: 19
<212> TYPE: PRT
<213> ORGANISM: Phyllomedusa bicolor
<220> FEATURE:
<221> NAME/KEY: LIPID
<222> LOCATION: (1)..(1)
<223> OTHER INFORMATION: MYRISTATE; amide linkage through amino group
      of N-terminal glycine.
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (19)..(19)
<223> OTHER INFORMATION: The carboxyl group of the C-terminal glutamine
      residue is amidated.

<400> SEQUENCE: 2

Gly Trp Met Ser Lys Ile Ala Ser Gly Ile Gly Thr Phe Leu Ser Gly
1               5                   10                  15

Met Gln Gln

<210> SEQ ID NO 3
<211> LENGTH: 32
<212> TYPE: PRT
<213> ORGANISM: Phyllomedusa bicolor

<400> SEQUENCE: 3

Ser Leu Gly Ser Phe Leu Lys Gly Val Gly Thr Thr Leu Ala Ser Val
1               5                   10                  15

Gly Lys Val Val Ser Asp Gln Phe Gly Lys Leu Leu Gln Ala Gly Gln
                20                  25                  30

<210> SEQ ID NO 4
<211> LENGTH: 32
<212> TYPE: PRT
<213> ORGANISM: Phyllomedusa bicolor
<220> FEATURE:
<221> NAME/KEY: LIPID
<222> LOCATION: (1)..(1)
<223> OTHER INFORMATION: MYRISTATE; amide linkage through amino group
      of N-terminal serine.
<220> FEATURE:

-continued

```
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (11)..(12)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION

<400> SEQUENCE: 4

Ser Leu Gly Ser Phe Leu Lys Gly Val Gly Thr Thr Leu Ala Ser Val
1               5                   10                  15

Gly Lys Val Val Ser Asp Gln Phe Gly Lys Leu Leu Gln Ala Gly Gln
            20                  25                  30
```

POLYPEPTIDES FOR MICROBIAL DETECTION

CROSS REFERENCE TO RELATED APPLICATIONS

This application is a division of U.S. patent application Ser. No. 12/867,078, filed Feb. 12, 2009, now U.S. Pat. No. 8,497,353, which was a national stage filing under 35 U.S.C. 371 of PCT/US2009/033903, filed Feb. 12, 2009, which claims the benefit of U.S. Provisional Application Ser. No. 61/028,896, filed Feb. 14, 2008, the disclosure of which is incorporated by reference in their entirety herein.

This application has associated with it a sequence listing with the file name Sequence_Listing__63973US005.TXT, created Jan. 19, 2009. The sequence listing file contains 2,442 bytes and it is incorporated herein by reference in its entirety.

BACKGROUND

Cytolytic peptides or cytolysins previously have been used to release active agents or "payload" from liposomes or cells. The mode of action for such peptides involves perturbation of the liposome or cellular membrane. These peptides include toxins from insects, fish, antibiotic peptides and synthetic peptides such as melittin, alamethicin, gramicidin, magainin and pardaxin, GALA, KALA, hemagglutinin subunit HA-2. Natural potent cytolytic peptides are found widely from insects to mammals, particularly as antimicrobial peptides or defensins, where they are involved in innate defense at mucosal membranes and as cytolysins in lymphocytes. In order to target and localize the cytolytic action of such peptides, specific steps (e.g. activating synthesis, release from lysosomes, and cleavage of propeptides) are required. The biological delivery activity of such peptides is tightly controlled. Cytolysin activity is cloaked by sophisticated mechanisms.

The acceptance of diagnostic methods involving the use of cytolysins has been hindered by their inferior sensitivity and non specific variable background, compared to alternative methods. Liposomes have, previously, been utilized in homogenous assays using complement-mediated lysis (Anal. Biochem. 1 18 (198 1) 286-293). However, such assays are considered unreliable as they involve many labile components, any one of which may become inactivated, thereby eliminating payload release. Preservation of the stability and water solubility of the cytolytic peptides remain obstacles to their use in diagnostic applications.

For a reliable assay, the release of detectable marker molecules should only occur in response to an external trigger and any leakage of marker molecules should be minimal for example, approaching zero, or at least remain constant over the assay period. Consequently, in such assays there is always a danger of background signal or interference caused by the progressive release of marker molecules. There is a need for better control over the activity of cytolysins for a variety of diagnostic assays.

SUMMARY

The present disclosure relates to polypeptides that are capable of modulating the permeability of a lipid vesicle (e.g., cytolytic polypeptides). Preferably, the polypeptides comprise activatable groups which control the capability of the polypeptides to modulate the permeability of a lipid vesicle. The may be activated in response to environmental stimuli, such as a change in the pH of the environment. Alternatively, the polypeptide may serve as an enzyme substrate for an enzyme which hydrolyzes the activatable group, thereby controlling the capability of the polypeptide to modulate the permeability of a lipid vesicle. In certain preferred embodiments, the polypeptide comprises a plurality of activatable groups.

The present disclosure also relates to the use of said polypeptides in methods for detecting a target microorganism. The polypeptides may respond to metabolic activity of the target microorganism (e.g., the production of acidic metabolites or the synthesis of an enzyme which can activate the polypeptide.

In one aspect, the present disclosure includes a polypeptide for the release of a substance from a lipid vesicle. The polypeptide can comprise an activatable pore-forming portion which, when activated modulates the permeability of the lipid vesicle. The polypeptide further can comprise at least three phosphate groups. The hydrolysis of at least one of the phosphate groups can activate the pore-forming portion of the polypeptide.

In another aspect, the present disclosure includes a purified polypeptide comprising SEQ ID No. 1, with at least one phosphate group attached thereto. The present disclosure further includes compositions comprising the purified polypeptide comprising SEQ ID No. 1 with at least one phosphate group attached thereto and a lipid vesicle comprising a signaling element which generates a detectable signal.

In another aspect, the present disclosure includes a purified polypeptide comprising SEQ ID No. 2, with at least one phosphate group attached thereto. The present disclosure further includes compositions comprising the purified polypeptide comprising SEQ ID No. 2 with at least one phosphate group attached thereto and a lipid vesicle comprising a signaling element which generates a detectable signal.

In another aspect, the present disclosure includes a purified polypeptide comprising SEQ ID No. 3, with at least one phosphate group attached thereto. The present disclosure further includes compositions comprising the purified polypeptide comprising SEQ ID No. 3 with at least one phosphate group attached thereto and a lipid vesicle comprising a signaling element which generates a detectable signal.

In another aspect, the present disclosure includes a purified polypeptide comprising SEQ ID No. 4, with at least one phosphate group attached thereto. The present disclosure further includes compositions comprising the purified polypeptide comprising SEQ ID No. 4 with at least one phosphate group attached thereto and a lipid vesicle comprising a signaling element which generates a detectable signal.

In another aspect, the present disclosure includes a method for detecting a target microorganism in a sample. The method comprises providing a sample, a lipid vesicle comprising a signaling element which generates a detectable signal, and a polypeptide. The polypeptide can comprise an activatable pore-forming portion which, when activated modulates the permeability of the lipid vesicle. The polypeptide further can comprise at least three phosphate groups. The method further comprises providing contact between the sample, the lipid vesicle, and the polypeptide; and detecting the detectable signal.

In another aspect, the present disclosure includes a method for detecting a target microorganism. The method comprises providing a sample, a lipid vesicle comprising a signaling element which generates a detectable signal, a culture device including a culture medium, and a polypeptide. The polypeptide can comprise an activatable pore-forming portion which, when activated modulates the permeability of the lipid vesicle. The polypeptide further can comprise at least three phosphate groups. The method further can comprise providing contact between the sample and the culture medium under conditions which permit the metabolic activity of a target microorganism, if present in the sample. The method further can comprise providing contact between the sample, the lipid vesicle, and the polypeptide under conditions that position the lipid vesicle in proximity to the target microorganism, if present; and detecting the detectable signal.

As used herein, the terms "analyte" and "antigen" are used interchangeably and refer to various molecules (e.g., zymosan) or epitopes of molecules (e.g., different binding sites of zymosan), or whole cells of the microorganism, that are characteristic of a microorganism (i.e., microbe) of interest. These include components of cell walls (e.g., cell-wall proteins), external cell wall components (e.g., mannan, chitin, or zymosan), internal cell components (e.g., cytoplasmic membrane proteins), etc.

The term "signaling element" refers to molecules or compositions which function to provide a detectable signal (e.g., absorbance of light, reflectance of light, fluorescence, luminescence, conductivity, impedance, and the like). Signaling elements may be "manifest signaling elements", such that they can provide an immediate and/or obvious detectable signal (e.g., a fluorescent dye). Alternatively, signaling elements may be "latent signaling elements", such that they must be activated in order to provide a detectable signal.

The term "recognition element" refers to a molecule which recognizes and selectively binds to an analyte. Recognition elements include, for example antibodies and the antigen-binding sites derived therefrom. Recognition elements also include receptors and the receptor binding sites derived therefrom. The term "capture agent", as used herein, refers to a recognition element attached to a support material (e.g., a particle, a substrate, a membrane, a fiber, a hydrogel, etc.).

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a sample suspected of containing "a" lipid vesicle can be interpreted to mean that the sample can include "one or more" lipid vesicles.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

DETAILED DESCRIPTION

The present disclosure relates to compositions and methods for rapidly detecting a microorganism. The methods include the use of an activatable polypeptide which, when activated, can modulate the permeability of a lipid vesicle. Preferably, the polypeptide comprises a plurality of similar activatable groups, which may be activated in a similar manner. Activatable polypeptides are disclosed in International Publication No. WO99/020252, entitled "PARTICLES", and in International Publication No. WO02/059147, entitled "ARMED PEPTIDES", which are incorporated herein by reference in their entirety. Table 1 shows a list of polypeptides which can disrupt the permeability of a lipid vesicle (e.g., a cell or a liposome). Methods of using an activatable polypeptide to detect a target microorganism are described in PCT Publication No. WO2009/102824 and entitled "METHODS AND COMPOSITIONS FOR DETECTING MICROORGANISMS", which is incorporated herein by reference in its entirety.

TABLE 1

Peptides which can disrupt the permeability of liposomes.

A-23187 (Calcium ionophore)
Aerolysin
Amphotericin B
Ascaphin
*Aspergillus* haemolysin
Alamethicin
Apolipoproteins
ATP Translocase
Bombinin
Brevinin
Buforin
Caerin
Cereolysin
Colicins
Dermadistinctin
Dermaseptin
Dermatoxin
Direct lytic factors from animal venoms
Diphtheria toxin
Distinctin
Esculetin
Filipin
Gaegurin
GALA
Gramicidin
Helical erythrocyte lysing peptide
Hemolysins
Ionomycin
KALA
LAGA
Listeriolysin
Maculatin
Magainin
Maxymin
Melittin
Metridiolysin
Nigericin
Nystatin
Ocellatin
P25
Palustrin
Phospholipases
Phylloxin TABLE 1-continued Peptides which can disrupt the permeability of liposomes.

Polyene Antibiotics
Polymyxin B
Ranalexin
Ranateurin
Rugosin
Saponin
*Staphylococcus aureus* toxins (α, β, χ, δ)
Streptolysin O
Streptolysin S
Synexin
Surfactin
Tubulin
Valinomycin
Vibriolysin In some embodiments, the activatable polypeptide may be a polypeptide (e.g., a cytolytic peptide) which comprises an activatable structure, such as a chemical bond or constituent. The activatable structure, when activated, can enhance the capability of the polypeptide to modulate the permeability of a membrane. In some embodiments, the activatable structure may be a chemical constituent, such as a phosphate group (e.g., a phosphate ester), which is responsive to pH. For example, protonation of the phosphate group may activate the cytolytic activity of the signal-generating element. Such protonation may be mediated by the metabolic activity (e.g. production of acidic metabolites) of the target microorganisms. Several exemplary cytolytic peptides, GALA and LAGA, become activated as the pH drops from 7 to about 5.0 (Advanced Drug Delivery Reviews 56, (2004) 967-985). Conversely, another cytolytic peptide, KALA, is activated as the pH is raised from 5 to about 7.5. International Publication No. WO2002/059147 discloses some peptides which are activated between 6.5 and 7.4, and other peptides which are triggered below 6.0, or 5.5.

In alternative embodiments, the activatable structure by activated by hydrolysis of a chemical bond, such as a phosphate ester. Hydrolysis of the bond may, for example, reduce the polarity (hydrophilicity) of the cytolytic peptide and/or may alter the isoelectric point of the peptide and thereby cause the polypeptide to modulate the permeability of a membrane. Such hydrolysis of a bond may be mediated by the metabolic activity (e.g. a phosphatase enzyme activity) of the target microorganism.

In certain embodiments, the polypeptide comprises a plurality of activatable groups (e.g., phosphate groups) which may be activated in a similar manner (e.g., by a pH change or by hydrolysis of the group by an enzyme activity such as phosphatase enzyme activity. The polypeptide may comprise at least three activatable groups, at least four activatable groups, at least five activatable groups, or at least six activatable groups. When the polypeptide comprises the plurality of activatable groups in an unactivated state, the polypeptide has a decreased capability to modulate the permeability of a lipid vesicle. When the polypeptide comprises a plurality of the activatable groups, the conversion of at least two of the activatable groups into an activated state, at least three of the activatable groups into an activated state, at least four of the activatable groups into an activated state, at least six of the activatable groups into an activated state, or all of the activatable groups into an activated state, gives the polypeptide an increased capability to modulate the permeability of a lipid vesicle.

Cytolytic peptides may be synthesized with activatable groups. Methods to synthesize polypeptides are known in the art (see, for example, "Fmoc Solid Phase Peptide Synthesis, A Practical Approach", W. C. Chan and P. D. White, eds., Oxford University Press, New York, N.Y.) Amino acids such as serine and threonine have a side chain comprising an alcohol group (—$CH_2OH$). The alcohol groups can form ester bonds with a phosphate group ($H_3PO_4$), for example. Serine-phosphate esters and threonine-phosphate esters are two examples of activatable groups for a cytolytic peptide. Such groups can be incorporated into a synthetic polypeptide by using N-a-Fmoc-O-benzyl-L-phosphoserine and N-a-Fmoc-O-benzyl-L-phosphothreonine, respectively, to synthesize the polypeptide, as described below.

The present disclosure includes cytolytic peptides comprising amino acid sequences with a plurality of serine and threonine amino acid residues. In certain preferred embodiments, the amino acid sequence includes at least three, at least four, at least five, or at least six serine or threonine residues or combinations of serine and threonine residues. Table 2 shows the amino acid sequences of two exemplary cytolytic peptides with combinations of at least four serine and threonine residues. SEQ ID No. 1 shows the primary amino acid sequence of the cytolytic peptide phylloxin, which is a naturally-occurring antimicrobial peptide found in the dermal secretions of the Giant Leaf Frog. The amino acid sequence of phylloxin comprises three serine residues and one threonine residues, each of which can be modified with a phosphate ester, as shown in SEQ ID No. 2. SEQ ID No. 3 shows the primary amino acid sequence of the cytolytic peptide dermatoxin, which is also a naturally-occurring antimicrobial peptide found in dermal secretions of the Giant Leaf Frog. The amino acid sequence of dermatoxin comprises four serine residues and two threonine residues, each of which may be modified with a phosphate ester.

TABLE 2

Amino acid sequences for phylloxin (SEQ ID Nos. 1 and 2) and dermatoxin (SEQ ID No. 3). The sequences are shown with the N-terminus on the left and the C-terminus on the right. Note: Although the primary amino acid sequences are similar in SEQ ID Nos. 1 and 2, all three of the serine (S) residues and the single threonine (T) reside in SEQ ID No. 2 are phosphorylated. Similarly, all serine and threonine residues in SEQ ID No. 4 are phosphorylated.

| Polypeptide | Amino Acid Sequence |
|---|---|
| SEQ ID No. 1 | GWMSKIASGIGTFLSGMQQ |
| SEQ ID No. 2 | GWMSKIASGIGTFLSGMQQ |
| SEQ ID No. 3 | SLGSFLKGVGTTLASVGKVVSDQFGKLLQAGQ |
| SEQ ID No. 4 | SLGSFLKGVGTTLASVGKVVSDQFGKLLQAGQ |

Methods of Detection

In one aspect, the present disclosure provides methods for the detection of target microorganisms in a non-growth dependent assay. As used herein, "non-growth dependent assay" refers to a test for target microorganisms that does not include a step wherein growth nutrients are provided and an incubation step is performed under conditions that are intended to cause the growth and multiplication of the target microorganisms. It should be noted that, although the non-growth dependent assays do not require a growth step as a component of the method, a non-growth dependent assay may be preceded by a growth step, which may improve the ability to detect relatively low numbers of target microorganisms.

Figure 1:
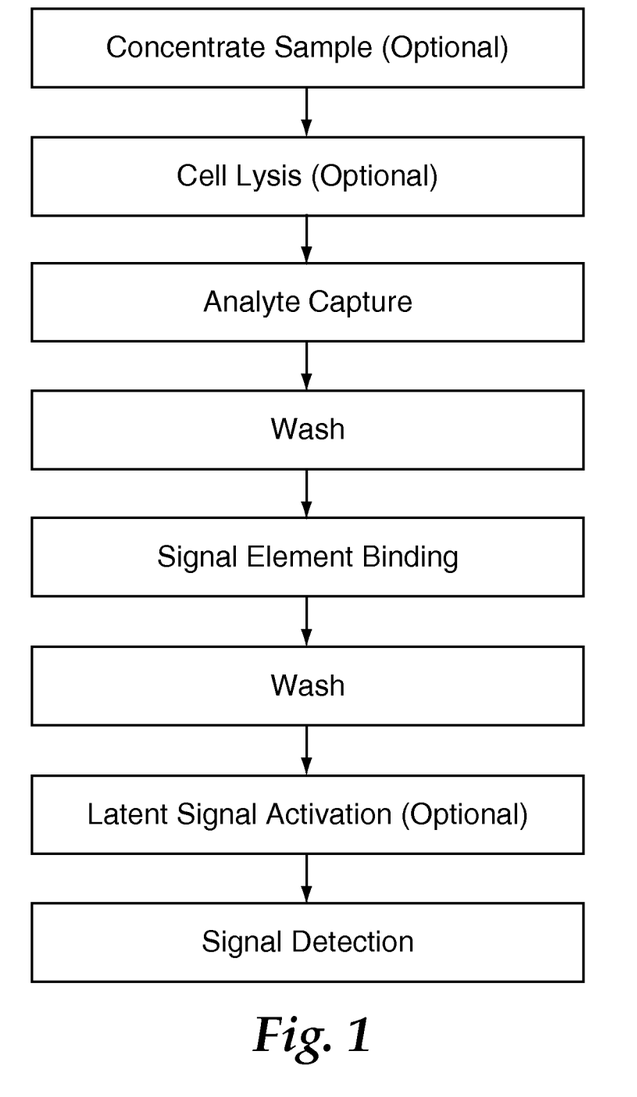
FIG. 1 is a block diagram of a method using a capture agent for detecting a target microorganism in a sample.

FIG. 1 shows a block diagram of an exemplary non-growth dependent assay. In the illustrated embodiment, the sample optionally may be concentrated (e.g., by filtration or centrifugation). The sample optionally may be treated with a lysing agent to enhance the interaction between the recognition element (e.g., an antibody) and its corresponding binding partner (e.g. a cell wall component such as zymosan). Suitable lysing agents may include chemical agents such as detergents and/or physical agents such as heat or ultrasonic vibration. After the concentration step and/or the lysis step, if either is desired, the target microorganism (or component thereof) is contacted with a capture agent attached to a support material under conditions effective to capture one or more analytes characteristic of one or more fungal microorganisms, if present in the sample, to form one or more captured analytes. In some embodiments, the analytes are cell surface components of an intact microorganism. The captured analytes are contacted with recognition elements and their corresponding signaling elements under conditions effective to cause binding between the captured analytes, the recognition elements and signaling elements. It should be noted also that the lysis step, the target capture step, and the step of binding the recognition and signaling elements may be conducted separately or in combinations of two or more of the individual steps.

Following the binding steps, the support material can be washed to remove nonspecifically bound and/or unbound signaling element. Following the wash step, the latent signaling element, if one is present in the assay, can be activated to produce a detectable signal. Activation can include, for example, the addition of an enzyme substrate to the mixture and/or the disruption of a lipid vesicle by chemical or physical means. The detectable signal can be detected to determine the presence of the target microorganism in the sample. Optionally, the detectable signal can be measured and the number of target microorganisms in the original sample can be estimated.

Figure 2:
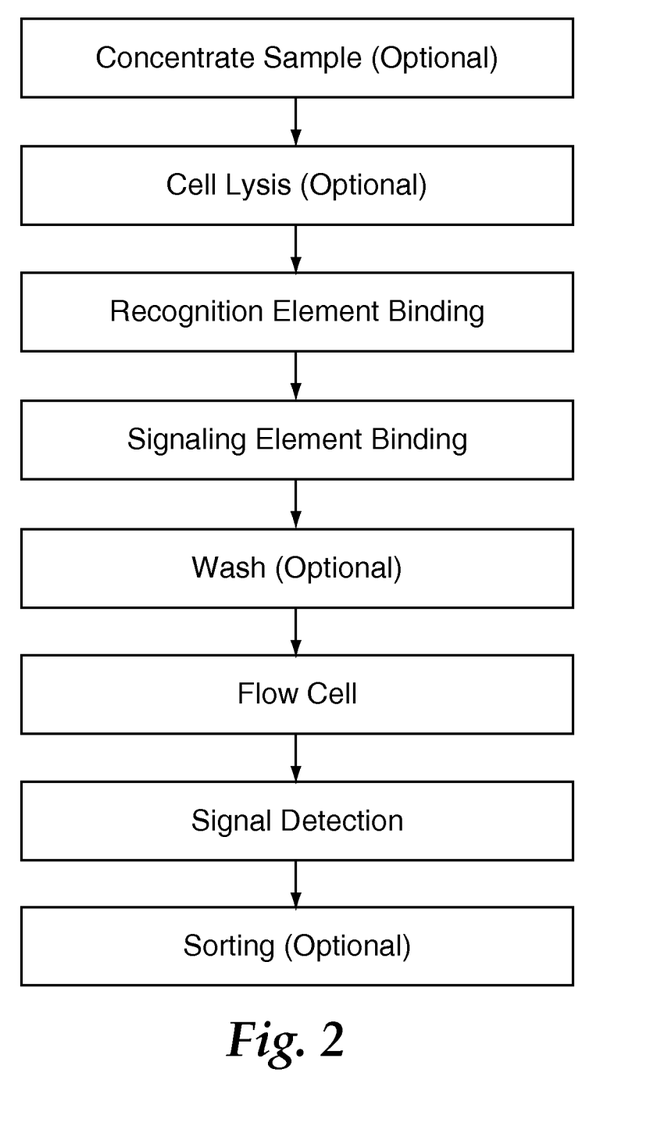
FIG. 2 is a block diagram of a method for detecting a target microorganism in a sample.

FIG. 2 shows a block diagram of an alternative exemplary non-growth dependent assay. In the illustrated embodiment, the sample optionally may be concentrated (e.g., by filtration or centrifugation). The sample optionally may be treated with a lysing agent to enhance the interaction between the recognition element and its corresponding binding partner (e.g. a cell wall component such as zymosan). Suitable lysing agents may include chemical agents such as detergents and/or physical agents such as heat or ultrasonic vibration.

After the concentration step and/or the lysis step, if either one of those steps is included, the target microorganism (or component thereof) can be contacted with recognition elements and their corresponding signaling elements under conditions effective to cause binding between the target microorganism, if at least one is present, the recognition elements, and signaling elements. The mixture may be washed to remove signaling element that may be nonspecifically bound to the nontarget microorganisms, although the method including fluorescent particles (described below) shows that the wash step can be optional. The mixture can be passed through a flow system, such as a flow cytometer, with a detector. Optionally, the sample may be contacted with a capture agent bound to a support material under conditions effective to cause binding between a target microorganism and the capture agent. In some embodiments, the support material may be a fluorescent particle which fluoresces at a first wavelength.

The captured material can be contacted with a recognition element labeled with a signaling element (e.g., comprising a fluorescent dye which fluoresces at a second wavelength) under conditions effective to cause binding between the recognition element and a captured target microorganism (or component thereof), if one is present. The support material can then be passed through a flow system such as a flow cytometer. Thus, in some embodiments, the detection of a fluorescent particle in the flow cell which fluoresces at both the first and second wavelengths may indicate the presence of a target microorganism in the sample. Optionally, in the flow cell system, the particles may be sorted and the positive particles may be subjected to confirmatory testing such as polymerase chain reaction (PCR) testing or culture methods, for example.

In another aspect, the present disclosure provides methods for the detection of target microorganisms in a growth-dependent assay. Growth dependent assays include a step to increase the number of target microorganisms by providing an environment (e.g., nutrients, temperature) which enables the target microorganisms to undergo growth, metabolism, and/or cell division.

FIG. 2 shows a block diagram of an exemplary growth-dependent assay. In the illustrated embodiment, the sample optionally may be concentrated (e.g., by filtration or centrifugation) prior to the growth step. The sample can be placed into a culture device containing a nutrient medium. The nutrient medium and the incubation temperature can be chosen according to the growth requirements of the target microorganism. The nutrient medium can be contained in a variety of culture devices, such as petri dishes, rehydratable culture devices (e.g., film culture devices sold by 3M Company, St. Paul, Minn., under the trade name PETRIFILM), microtiter plates, flasks, tubes, and the like.

Prior to the growth step or, optionally, after the growth step, the recognition and signaling elements can be added to the sample mixture under conditions effective to cause the binding of the recognition and signaling elements to the target microorganisms (or components thereof). In this embodiment, a latent signaling element, which is activated by a metabolic activity of the target microorganisms, can be used. For example, the latent signaling element can include a signal-generating element (e.g., cytolytic peptides such as those described in International Publication Nos. WO99/020251 or WO2002/059147. Such cytolytic peptides form pores in lipid vesicles when the pH of the environment is altered (e.g., by the metabolism of nutrients to acidic byproducts), thereby making the vesicle membrane permeable. Alternatively, functional groups, such as phosphate groups, on the cytolytic peptides may be hydrolyzed, thereby permitting the formation of pores in the lipid vesicle. Yeast and mold microorganisms are known to produce phosphatase enzymes which could be used in the activation of a cytolytic peptide. After activation of the latent signaling element, the signal can be detected.

Figure 3:
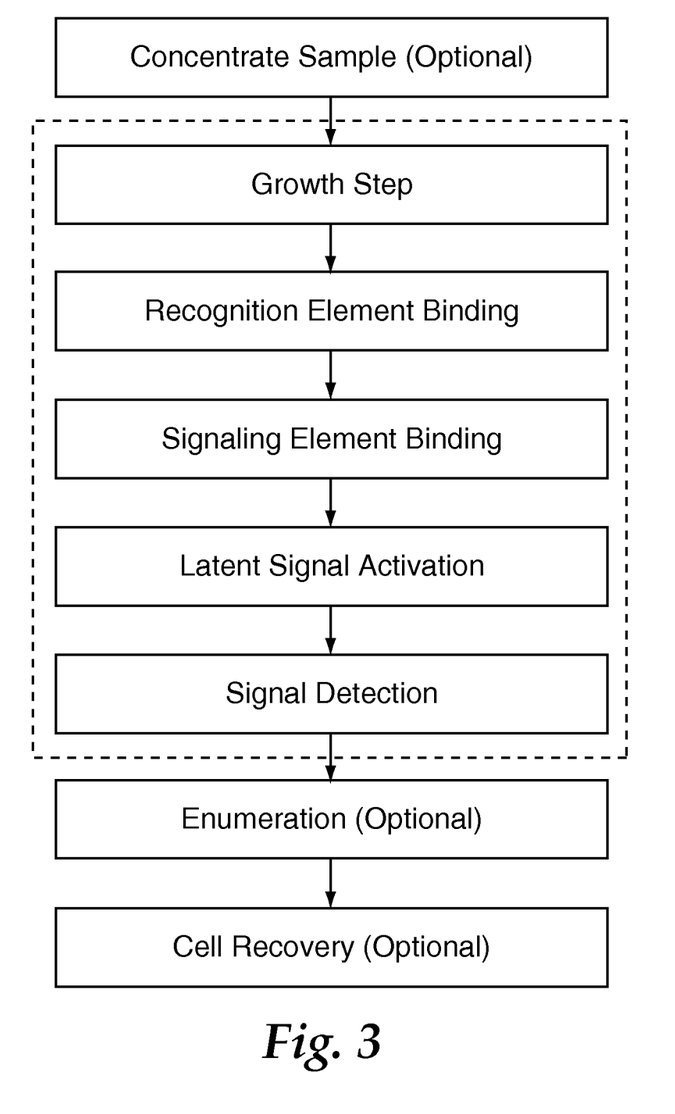
FIG. 3 is a block diagram of a method using a growth step for the detection of a target microorganism in a sample.

In some embodiments involving nutrient growth medium, the individual target microorganisms from the sample may be spatially separated (e.g., on the surface of an agar plate) such that the location of individual colonies or microcolonies (after the growth and signal detection steps) may be observed. Embodiments including spatial separation of the target microorganisms from the original sample may include an optional enumeration step wherein the individual colonies or microcolonies are counted. A further optional step may include the recovery of target microorganisms (e.g., picking a colony) for subsequent archiving or additional testing (e.g., PCR analysis). It should be recognized that some of the steps in the growth-dependent assay may be performed simultaneously. For example, the steps shown in the dashed box in FIG. 3 may be performed simultaneously, relying on the metabolic activity of the growing cells to activate the latent signal. When the indicated steps are performed simultaneously, it may be possible to monitor the culture device continuously or at various times to observe detectable signals. This process could provide for early detection of target microorganisms.

Preferably, in the above-described methods, providing contact between the sample, the immobilized antibodies, and the labeled recognition elements (e.g., antibodies) includes: contacting the sample with the immobilized antibodies under conditions effective to capture one or more analytes characteristic of a specific target microorganism, if present in the sample, to form one or more captured analytes; and contacting the one or more captured analytes, if present, with the labeled recognition elements under conditions effective to cause binding between the one or more captured analytes and the labeled recognition elements. Preferably, contacting the sample with the capture agents includes providing contact between the sample and each capture agent simultaneously. Preferably, contacting the one or more captured target microorganisms, if present, with the labeled recognition elements includes providing contact between the captured target microorganisms and each labeled recognition element simultaneously.

Samples

In certain embodiments, the fluid samples comprise a food or beverage. Methods for the preparation of food samples for microbiological analyses are well known. Some of the sample preparation methods for food samples involve suspending a known quantity of food material (25 grams, for example) in a relatively large volume of diluent (225 milliliters, for example). The sample is subjected to a strenuous mixing process, such as blending or stomaching, to create a relatively homogeneous liquid suspension. The samples are frequently processed in a plastic sample reservoir which is called a stomacher bag. Methods and compositions of the present disclosure provide a way to analyze food or beverage samples. Nonlimiting examples of foods which are routinely tested for microorganisms include meat (e.g., ground meat, poultry, fish, seafood), fresh or processed produce (e.g., fruit, vegetables), dairy (e.g., milk or milk products, whey, cheese), and beverages (e.g., milk, water, fruit juices, vegetable juices, tea).

In some embodiments, samples to be processed and analyzed include samples from a body of water. Nonlimiting examples of such bodies of water include surface water, water for human or animal consumption, and water used for industrial processes. Surface water includes an ocean, a lake, a river, a canal, a pond, a reservoir, a stream, and the like. Process water includes water that is used in municipal or industrial purposes, such as cleaning, washing, rinsing, cooling towers, water treatment holding tanks, and the like. Exemplary cleaning processes include food processing processes, such as, washing, rinsing, and disinfecting meat or produce for human or animal consumption.

In other embodiments, the methods and compositions of the present disclosure are used to analyze samples that are amenable to processing and microbial detection such as, for example, solutions, mixtures, homogenates, or liquid suspensions of foodstuffs, beverages and pharmaceutical products. In certain embodiments, the liquid sample comprises one or more dissolved solute, such as sugars, salts, or proteins. In other embodiments, the liquid sample may comprise one or more solvent, such as an alcohol, or a surfactant. Samples with solvents or surfactants can be used in accordance with the present invention, provided the solvents or surfactants are present at a concentration which does not prevent the detection of the detectable signal or cause the inadvertent conversion of a latent signaling element to a detectable signal (e.g., causing a detectable signal when there are no target microorganisms present in the sample). Samples which, when mixed with pH-sensitive signaling elements (e.g., a fluorescent label such as methylumbelliferone) or pH-responsive signal-generating elements (e.g., pH-triggered cytolytic peptides), may be buffered and/or adjusted to a compatible pH prior to mixing with the pH-sensitive or pH-responsive elements.

In some embodiments, the methods and compositions of the present disclosure can be used to detect microorganisms in an environmental or clinical sample. Typically, environmental or clinical samples are collected using a swab, a sponge, a wipe, or the like to collect residual material from a surface (e.g., a counter top, a floor, skin, a wound site) which may be contaminated with microorganisms. The collection device can be transferred to a sample reservoir, such as a stomacher bag, and mixed or homogenized with a solvent (e.g., Standard Methods Buffer, buffered peptone water, buffered saline, or distilled water) to release the microorganisms into the solvent. Subsequently, the solvent can be analyzed for the presence of a microorganism. Alternatively, the target microorganisms may be analyzed in a solution containing the collection device.

Individual liquid samples may contain almost any number and kind of microorganism. The number of microorganisms in a liquid sample may range from zero organisms per milliliter, in a sample that has been subjected to sterilizing conditions, up to approximately $10^9$ or more organisms per milliliter in a heavily-contaminated sample. The devices and methods of the present invention provide for the analysis of liquid samples containing a wide variety of microbial concentrations.

EXAMPLES

Example 1

Synthesis of Tetraphosphorylated Phylloxin

The fully phosphorylated phylloxin was prepared using an Applied Biosystems 433A Peptide Synthesizer (Applied Biosystems, Foster City, Calif.) and Fmoc-protected amino acids on Rink amide resin. Phosphorylated serine and threonine were introduced as the phosphorylated amino acids, using N-a-Fmoc-O-benzyl-L-phosphoserine and N-a-Fmoc-O-benzyl-L-phosphothreonine, respectively (EMD Biosciences, La Jolla, Calif.) using the procedures described in "Fmoc Solid Phase Peptide Synthesis, A Practical Approach", W. C. Chan and P. D. White, eds., Oxford University Press, New York, N.Y. The N-terminal of the peptide was capped with myristic acid using standard peptide synthesis conditions. After the peptide synthesis was complete, the crude peptide was deprotected and cleaved from the Rink amide resin using a solution of trifluoroacetic acid:water: phenol:triisopropylsilane (88:5:5:2). The crude peptide was precipitated in cold diethylether and collected by centrifugation.

The synthesized polypeptide was purified by HPLC on a Luna 5µ C18 column (Phenomenex, Torrance, Calif.) using a linear gradient elution. The gradient started with a ratio of 94.5:5.0:0.5 water:acetonitrile:trifluoroacetic acid (TFA) and ended with a ratio of 5.0:94.5:0.5 water: acetonitrile:TFA over a 15 minute running time. The structure and formula weight of the purified product was verified by mass spectroscopy.

Example 2

Activation of Tetraphosphorylated Phylloxin to Cause Permeabilization of Liposomes This experiment demonstrates the formation of pores in liposomes with a horseradish peroxidase/glucose oxidase couple. The formation of a pore allows glucose into the liposome where it reacts with glucose oxidase to generate hydrogen peroxide. The hydrogen peroxide reacts with HRP, 4-AAP and TOOS (all outside the liposome) to generate an intense purple color.

A. Synthesis of DPPC Liposomes Containing Glucose Oxidase 6.25 ml of a 20 mg/ml $CHCl_3$ solution of 1,2-dipalmitoyl-sn-glycero-3-phosphocholine (DPPC) (Avanti Polar Lipids, Alabaster, Ala.) was measured into a flask. The solution was dried on a rotary evaporator and placed under vacuum to remove excess solvent.

The dried lipid film was hydrated with 3 ml of a 5 mg/ml solution of glucose oxidase (GO) (EMD Biosciences, La Jolla, Calif.) in 50 mmol N-Tris(hydroxymethyl)methyl]-2-aminoethanesulfonic acid (TES), the pH of which was adjusted to 6.5 with 1 N HCl. The resulting suspension was placed in an ultrasonic bath (Bransonic 2510, Branson Ultrasonic Corp., Danbury, Conn.) and sonicated for one hour at 50° C. Following sonication the flask containing the liposome solution was alternately frozen in a dry ice/acetone bath and then thawed in warm water five times. The cloudy suspension was then extruded fifteen times through a 400 nm polycarbonate membrane (Avanti Polar Lipids) at 50°-55° C. The unencapsulated GO was removed from the liposome suspension by column chromatography twice through a stacked set of HiTrap desalting column, a Q-XL anion exchange column, and a SP-XL cation exchange column (all from GE Healthcare, Piscataway, N.J.). The lipid-containing fractions were combined and condensed by dialysis with a PEG-50 mM TES solution, and then chromatographed once more through ALL of the columns listed previously. The lipid concentration of Fraction 2 was collected and was assessed with a Phospholipid C test (Wako Chemicals, Richmond Va.). The Phospholipid C test showed a concentration of 2.5 mg/ml.

B. Synthesis of DOPC/Cholesterol Liposomes Containing Glucose Oxidase:

Cholesterol (21.2 mg) (Sigma-Aldrich, St. Louis, Mo.) and 1,2-dioleoyl-sn-glycero-3-phosphocholine (DOPC) (80.5 mg) (Avanti Polar Lipids, Alabaster, Ala.) were combined in a flask and dissolved in $CHCl_3$, then dried on a rotary evaporator and placed under vacuum to remove excess solvent.

The dried lipid film was then hydrated with 5 ml of a 5 mg/ml solution of glucose oxidase in 50 mmolar TES, pH 6.5. The resulting suspension was then placed in a Bransonic 2510 ultrasonic bath) and sonicated for one hour at 40° C.

Following sonication the flask containing the liposome solution was alternately frozen in a dry ice/acetone bath and then thawed in warm water five times. The cloudy solution was extruded fifteen times through a 400 nm polycarbonate membrane at 40° C., then a further fifteen times through a 200 nm membrane. The unencapsulated GO was removed by column chromatography through a stacked Q-XL anion exchange column and SP-XL cation exchange column. The lipid-containing fractions were combined and condensed by dialysis with a PEG-50 mM TES solution, and then chromatographed once more through all of the columns listed previously. The cloudy fractions were combined and lipid concentration was assessed with a Phospholipid C test and found to contain 7.4 mg/mL.

C. Activation of Tetraphosphorylated Phylloxin

The ability of the phosphorylated phylloxin to open liposomes in the presence of phosphatase was tested by preparing a developing solution of 0.5 mg/mL TOOS (3-(N-Ethyl-3-methylanilino)-2-hydroxypropanesulfonic acid sodium salt) (Sigma-Aldrich, St. Louis, Mo.), 1.0 mg/mL 4-AAP (4-amino-antipyrene) (Sigma-Aldrich), 12.5 mg/mL glucose and 0.0001 mg/mL HRP (horseradish peroxidase) (Pierce Biotechnology, Rockford, Ill.) in 50 mM TES.

200 μL of this solution was placed in one well of 96-well plate containing 10 μL (0.004 mg/mL) of a DPPC liposome suspension. A second well was prepared similarly and 10 μL (0.3 mg/mL) of phylloxin solution in TES was also added. A third well was prepared similar to the second well. Alkaline phosphatase (10 μL at 2.5 mg/mL in TES) was added to the third well to a final concentration of 0.11 mg/mL. A similar set of wells was prepared with DOPC/cholesterol liposomes at the same concentration.

After 30 minutes at room temperature, a dark purple color was apparent in the well with DOPC/cholesterol liposomes, phylloxin and phosphatase. A weaker color was apparent in the well with DPPC liposomes, phylloxin and phosphatase, and weaker again in the well with DPPC liposomes and phylloxin. The remaining wells were essentially colorless. The image was recorded on an HP scanner and analyzed using an AlphaImager (Alpha Innotech, San Leandro, Calif.). The integrated digital values at 30 minutes are shown in Table 1 below, and at two hours in Table 2. This data shows that with DOPC/cholesterol liposomes phylloxin rapidly opens liposomes in the presence of alkaline phosphatase, but has little effect in its absence. With DPPC liposomes, there is still an effect, but it is not so pronounced.

TABLE 1

Relative glucose oxidase activity in each well after a 30-minute incubation.

|  | DPPC | DOPC/Cholesterol |
|---|---|---|
| Liposome only | 60816 | 60816 |
| Liposome + peptide | 84996 | 67680 |
| Liposome + peptide + phosphatase | 97588 | 184416 |

TABLE 2

Relative glucose oxidase activity in each well after a 2-hour incubation.

|  | DPPC | DOPC/Cholesterol |
|---|---|---|
| Liposome only | 76084 | 84354 |
| Liposome + peptide | 173670 | 128550 |
| Liposome + peptide + phosphatase | 217620 | 299950 |

Example 3

Synthesis of Hexaphosphorylated Dermatoxin

The fully phosphorylated dermatoxin was prepared using an Applied Biosystems 433A Peptide Synthesizer (Applied Biosystems, Foster City, Calif.) and Fmoc-protected amino acids on Rink amide resin. Phosphorylated serine and threonine were introduced as the phosphorylated amino acids, using N-a-Fmoc-O-benzyl-L-phosphoserine and N-a-Fmoc-O-benzyl-L-phosphothreonine, respectively (EMD Biosciences, La Jolla, Calif.) using the procedures described in "Fmoc Solid Phase Peptide Synthesis, A Practical Approach", W. C. Chan and P. D. White, eds., Oxford University Press, New York, N.Y. The N-terminal of the peptide was capped with myristic acid using standard peptide synthesis conditions. After the peptide synthesis was complete, the crude peptide was deprotected and cleaved from the Rink amide resin using a solution of trifluoroacetic acid:water:phenol:triisopropylsilane (88:5:5:2). The crude peptide was precipitated in cold diethylether and collected by centrifugation.

Matrix-Assisted Laser Desorption/Ionization Time-of-Flight Mass Spectrometry (MALDI-TOF) and High Performance Liquid Chromatography (HPLC-UV-MS) indicated substantially amounts (>50%) of lower molecular weight impurities.

Example 4

Activation of Phosphorylated Dermatoxin to Cause Permeabilization of Liposomes

DPPC liposomes containing 5 mg/mL glucose oxidase were prepared as described in Example 2. Glucose oxidase activity was measured in a coupled enzyme reaction with horseradish peroxidase as described in Example 2. The various solutions were quickly added to each of the wells of a microplate using a multichannel pipette and the reactions were started (at T=0 hours) with the addition to the wells of a solution containing glucose and 4-AAP.

The ability of the phosphorylated dermatoxin to open liposomes in the presence of phosphatase was tested by preparing a developing solution as described in Example 2. One hundred-fifty microliters of the developing solution was placed in each well of a 96-well microplate. To each column in the plate was added 20 μL of TES buffer containing one of the following concentrations of unpurified dermatoxin: 3.3 mg/mL, $3.3\times10^{-1}$ mg/mL, $3.3\times10^{-2}$ mg/mL, $3.3\times10^{-3}$ mg/mL, $3.3\times10^{-4}$ mg/mL, $3.3\times10^{-5}$ mg/mL, $3.3\times10^{-6}$ mg/mL, or $3.3\times10^{-7}$ mg/mL. Negative control wells contained TES buffer with no dermatoxin. Positive control wells buffer contained TES buffer with Triton X-100. Ten-microliter aliquots of the following concentrations of DPPC liposomes (containing 5 mg/mL glucose oxidase) were added to wells in duplicate rows: 0.1 mg lipid/mL, 0.02 mg lipid/mL, 0.004 mg lipid/mL, or plain buffer. To one of the duplicate rows was added 20 μL of 2.5 mg/mL alkaline phosphatase in TES. The other duplicate row received 20 μL of TES buffer. Thus the final dermatoxin concentration in the well varied from $3.3\times10^{-3}$ mg/mL to $3.3\times10^{-11}$ mg/mL, and the final lipid concentration in the well ranged from 0.005 mg lipid/mL to $2.0\times10^{-4}$ mg lipid/mL.

The absorbance was recorded at 538 nm on a SpectraMax M5 plate reader (Molecular Devices, Sunnyvale, Calif.) after two hours incubation at room temperature, and also after overnight incubation (approximately 18 hours). Since the absorbance of several wells was saturated, the overnight samples were diluted 1:10 with 50 mmol TES and the absorbance of the diluted samples was measured.

Absorbance values for individual wells are shown in Table 3. These data show that, with the exception of wells containing the highest concentration of the phosphorylated dermatoxin crude preparation, there was more permeabilization of the liposomes by the peptide in the presence of phosphatase than in the absence of phosphatase enzyme activity. The decrease in phosphatase-dependent liposome permeabilization at the highest concentrations of dermatoxin may be due to the impurity of the preparation and may be improved by subjecting the preparation to a purification process, such as the chromatography process described in Example 1. Alternatively, the non-phosphatase-dependent liposome permeabilization may be due to the formation of pore-forming structures by the phosphorylated peptides at relatively high concentrations of the peptides. This activity may be diminished at lower concentrations of the phosphorylated peptide.

TABLE 3

Cytolytic peptide activity of the phosphorylated dermatoxin. Experimental protocol is reported in Example 4. All data have been rounded to the third decimal position and are reported in absorbance units.

| | | Dermatoxin mass (mg) (reaction with phosphatase) | | | | | | | Dermatoxin mass (mg) (reaction without phosphatase) | | | | | | |
|---|---|---|---|---|---|---|---|---|---|---|---|---|---|---|---|
| Reaction Time | Lipid conc. | $3.3\times10^{-5}$ | $3.3\times10^{-6}$ | $3.3\times10^{-7}$ | $3.3\times10^{-8}$ | $3.3\times10^{-9}$ | Positive Control | Negative Control | $3.3\times10^{-5}$ | $3.3\times10^{-6}$ | $3.3\times10^{-7}$ | $3.3\times10^{-8}$ | $3.3\times10^{-9}$ | Positive Control | Negative Control |
| 2 hrs | 0 | 0.122 | 0.120 | 0.118 | 0.119 | 0.118 | 2.272 | 0.140 | 0.121 | 0.115 | 0.116 | 0.114 | 0.113 | 0.123 | 0.111 |
| 2 hrs | 0.004 | 0.204 | 0.197 | 0.130 | 0.126 | 0.126 | 0.132 | 0.114 | 0.200 | 0.161 | 0.119 | 0.111 | 0.115 | 0.210 | 0.112 |
| 2 hrs | 0.02 | 0.546 | 0.480 | 0.140 | 0.132 | 0.124 | 0.296 | 0.123 | 0.633 | 0.263 | 0.141 | 0.111 | 0.114 | 0.602 | 0.116 |
| 2 hrs | 0.1 | 2.034 | 1.473 | 0.173 | 0.136 | 0.134 | 0.557 | 0.127 | 1.521 | 0.759 | 0.267 | 0.132 | 0.121 | 2.220 | 0.128 |
| 18 hrs | 0 | 0.153 | 0.149 | 0.148 | 0.149 | 0.150 | 4.000 | 0.389 | 0.147 | 0.139 | 0.132 | 0.131 | 0.133 | 0.158 | 0.132 |
| 18 hrs | 0.004 | 0.494 | 0.494 | 0.287 | 0.240 | 0.243 | 0.158 | 0.146 | 0.499 | 0.410 | 0.169 | 0.141 | 0.139 | 0.524 | 0.138 |
| 18 hrs | 0.02 | 2.003 | 1.856 | 0.469 | 0.357 | 0.336 | 0.524 | 0.306 | 1.833 | 1.013 | 0.315 | 0.149 | 0.143 | 2.043 | 0.161 |
| 18 hrs | 0.1 | OR[1] | OR | 0.530 | 0.349 | 0.358 | 2.043 | 0.334 | 3.720 | 3.294 | 0.974 | 0.200 | 0.177 | OR | 0.222 |
| 18 hrs (d)[2] | 0 | 0.053 | 0.053 | 0.052 | 0.054 | 0.053 | 1.064 | 0.079 | 0.054 | 0.052 | 0.054 | 0.053 | 0.053 | 0.055 | 0.056 |
| 18 hrs (d) | 0.004 | 0.092 | 0.090 | 0.066 | 0.063 | 0.062 | 0.056 | 0.053 | 0.096 | 0.081 | 0.056 | 0.054 | 0.054 | 0.097 | 0.053 |
| 18 hrs (d) | 0.02 | 0.262 | 0.231 | 0.084 | 0.075 | 0.072 | 0.094 | 0.069 | 0.247 | 0.145 | 0.072 | 0.054 | 0.054 | 0.274 | 0.053 |
| 18 hrs (d) | 0.1 | 1.045 | 0.785 | 0.095 | 0.076 | 0.075 | 0.252 | 0.070 | 0.846 | 0.413 | 0.145 | 0.060 | 0.058 | 1.018 | 0.061 |

[1]"OR" designates that the reading was out of range of the instrument (i.e., the spectrophotometer reading was saturated).
[2]"(d) designates the readings from the 1:10-diluted 18-hour sample.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A method for detecting a target microorganism in a sample, comprising:
    providing a sample, a lipid vesicle comprising a signaling element which generates a detectable signal, and a polypeptide;
    contacting the sample, the lipid vesicle, and the polypeptide; and
    detecting the detectable signal;
    wherein the polypeptide comprises an activatable pore-forming portion which, when activated modulate the permeability of the lipid vesicle; and at least three phosphate groups;
    wherein hydrolysis of at least one of the at least three phosphate groups activates the pore-forming portion of the polypeptide.

2. The method of claim 1, wherein hydrolysis of at least two of the at least three phosphate groups activates the pore-forming portion of the polypeptide.

3. The method of claim 1, wherein hydrolysis of at least three of the at least three phosphate groups activates the pore-forming portion of the polypeptide.

4. The method of claim 1, wherein the polypeptide comprises SEQ ID No. 1 with at least three phosphate groups attached thereto.

5. The method of claim 1, wherein the polypeptide comprises SEQ ID No. 3 with at least three phosphate groups attached thereto.

6. The method of claim 1, wherein detecting the detectable signal comprises measuring the detectable signal.

* * * * *